United States Patent
Rice et al.

(10) Patent No.: US 7,029,403 B2
(45) Date of Patent: Apr. 18, 2006

(54) METAL WOOD CLUB WITH IMPROVED HITTING FACE

(75) Inventors: Scott A Rice, Solana Beach, CA (US); Nicholas M Nardacci, Bristol, RI (US)

(73) Assignee: Acushnet Company, Fairhaven, MA (US)

( * ) Notice: Subject to any disclaimer, the term of this patent is extended or adjusted under 35 U.S.C. 154(b) by 176 days.

(21) Appl. No.: 10/428,061

(22) Filed: May 1, 2003

(65) Prior Publication Data

US 2003/0195058 A1 Oct. 16, 2003

Related U.S. Application Data

(63) Continuation-in-part of application No. 09/551,771, filed on Apr. 18, 2000, now Pat. No. 6,605,007.

(51) Int. Cl.
*A63B 53/04* (2006.01)

(52) U.S. Cl. ............... 473/329; 473/345; 473/346; 473/349

(58) Field of Classification Search ........ 473/324–350, 473/290–291
See application file for complete search history.

(56) References Cited

U.S. PATENT DOCUMENTS

| | | |
|---|---|---|
| 1,318,325 A | 10/1919 | Klin |
| 1,319,233 A | 10/1919 | Mattern |
| 1,467,435 A | 9/1923 | Kinnear |
| 1,525,352 A | 2/1925 | Aitken |
| 1,543,691 A | 6/1925 | Beat |
| 1,582,836 A | 4/1926 | Link |
| 1,589,363 A | 6/1926 | Butchart |
| 1,595,589 A | 8/1926 | Tyler |
| 1,605,551 A | 11/1926 | Mattern |
| 1,699,874 A | 1/1929 | Buhrke |
| 1,704,119 A | 3/1929 | Buhrke |
| 1,704,165 A | 3/1929 | Buhrke |
| 1,720,867 A | 7/1929 | Webster et al. |
| 2,034,936 A | 3/1936 | Barnhart |
| 2,087,685 A | 7/1937 | Hackney |

(Continued)

FOREIGN PATENT DOCUMENTS

CN     1114911     1/1996

(Continued)

OTHER PUBLICATIONS

Golf Digest, Sep., 1982, p. 25.

(Continued)

*Primary Examiner*—Sebastiano Passaniti
(74) *Attorney, Agent, or Firm*—D. Michael Burns

(57) ABSTRACT

A golf club head having selectively oriented zones of relatively high flexural stiffness is disclosed. The hitting face is configured and dimensioned so that it includes an inner zone and a concentric intermediate zone. The inner zone has relatively high flexural stiffness and the intermediate zone has relatively lower flexural stiffness. The inner zone may have an elliptical shape or a substantially parallelogram shape. Preferably, the inner zone has a shape that comprises a major axis and a minor axis and the major axis aligns substantially in the direction of high heel to low toe. This arrangement of inner and intermediate zones creates a gradient of flexural stiffness in the direction of high toe to low heel and produces a desirable manipulation COR in that direction. This area of high coefficient of restitution advantageously coincides with the ball impact pattern that golfers typically make on the hitting face. The hitting face also comprises a measurement zone wherein the lowest COR is at least 93% of the highest COR.

9 Claims, 7 Drawing Sheets

U.S. PATENT DOCUMENTS

| | | | |
|---|---|---|---|
| 3,567,228 | A | 3/1971 | Lynn |
| 3,571,900 | A | 3/1971 | Hardesty |
| 3,625,518 | A | 12/1971 | Solheim |
| 3,659,855 | A | 5/1972 | Hardesty |
| 3,863,932 | A | 2/1975 | Lezatte |
| 3,985,363 | A | 10/1976 | Jepson et al. |
| 4,023,802 | A | 5/1977 | Jepson et al. |
| 4,193,601 | A | 3/1980 | Reid, Jr. et al. |
| 4,213,613 | A | 7/1980 | Nygren |
| 4,214,754 | A | 7/1980 | Zebelean |
| D267,965 | S | 2/1983 | Kobayashi |
| 4,429,879 | A | 2/1984 | Schmidt |
| 4,432,549 | A | 2/1984 | Zebelean |
| 4,449,707 | A | 5/1984 | Hayashi et al. |
| 4,451,041 | A | 5/1984 | Hayashi et al. |
| 4,451,042 | A | 5/1984 | Hayashi et al. |
| 4,465,221 | A | 8/1984 | Schmidt |
| 4,471,961 | A | 9/1984 | Masghati et al. |
| 4,489,945 | A | 12/1984 | Kobayashi |
| 4,511,145 | A | 4/1985 | Schmidt |
| 4,762,324 | A | 8/1988 | Anderson |
| 4,792,140 | A | 12/1988 | Yamaguchi et al. |
| 4,804,188 | A * | 2/1989 | McKee et al. ............... 473/342 |
| 4,826,172 | A | 5/1989 | Antonious |
| 4,842,243 | A | 6/1989 | Butler |
| 4,884,808 | A * | 12/1989 | Retzer ..................... 473/288 |
| 4,913,438 | A | 4/1990 | Anderson |
| 4,915,385 | A | 4/1990 | Anderson |
| 4,915,386 | A | 4/1990 | Antonious |
| 4,919,430 | A | 4/1990 | Antonious |
| 4,919,431 | A | 4/1990 | Antonious |
| 4,921,252 | A | 5/1990 | Antonious |
| 4,928,965 | A | 5/1990 | Yamaguchi et al. |
| 4,930,781 | A | 6/1990 | Allen |
| 4,932,658 | A | 6/1990 | Antonious |
| 4,955,610 | A | 9/1990 | Creighton et al. |
| D312,858 | S | 12/1990 | Anderson et al. |
| 5,000,454 | A | 3/1991 | Soda |
| 5,024,437 | A | 6/1991 | Anderson |
| 5,028,049 | A | 7/1991 | McKeighen |
| 5,046,733 | A | 9/1991 | Antonious |
| 5,056,705 | A | 10/1991 | Wakita et al. |
| 5,060,951 | A | 10/1991 | Allen |
| 5,067,715 | A | 11/1991 | Schmidt et al. |
| 5,090,702 | A | 2/1992 | Viste |
| 5,094,383 | A | 3/1992 | Anderson et al. |
| 5,106,094 | A | 4/1992 | Desbiolles et al. |
| 5,141,230 | A | 8/1992 | Antonious |
| 5,163,682 | A | 11/1992 | Schmidt et al. |
| 5,180,166 | A | 1/1993 | Schmidt et al. |
| 5,183,255 | A | 2/1993 | Antonious |
| 5,213,328 | A | 5/1993 | Long et al. |
| 5,221,087 | A | 6/1993 | Fenton et al. |
| 5,240,252 | A | 8/1993 | Schmidt et al. |
| 5,242,167 | A | 9/1993 | Antonious |
| 5,255,918 | A | 10/1993 | Anderson et al. |
| 5,261,663 | A | 11/1993 | Anderson |
| 5,261,664 | A | 11/1993 | Anderson |
| 5,271,621 | A | 12/1993 | Lo |
| 5,292,129 | A | 3/1994 | Long et al. |
| 5,295,689 | A | 3/1994 | Lundberg |
| 5,301,945 | A | 4/1994 | Schmidt et al. |
| 5,318,300 | A | 6/1994 | Schmidt et al. |
| 5,328,184 | A | 7/1994 | Antonious |
| 5,344,140 | A | 9/1994 | Anderson |
| 5,346,218 | A | 9/1994 | Wyte |
| 5,351,958 | A | 10/1994 | Helmstetter |
| 5,358,249 | A | 10/1994 | Mendralla |
| 5,362,047 | A | 11/1994 | Shaw et al. |
| 5,362,055 | A | 11/1994 | Rennie |
| 5,366,223 | A | 11/1994 | Werner et al. |
| 5,380,010 | A | 1/1995 | Werner et al. |
| 5,390,924 | A | 2/1995 | Antonious |
| 5,395,113 | A | 3/1995 | Antonious |
| 5,397,126 | A | 3/1995 | Allen |
| 5,401,021 | A | 3/1995 | Allen |
| 5,405,136 | A | 4/1995 | Hardman |
| 5,405,137 | A | 4/1995 | Vincent et al. |
| 5,407,202 | A | 4/1995 | Igarashi |
| RE34,925 | E | 5/1995 | McKeighen |
| 5,417,419 | A | 5/1995 | Anderson et al. |
| 5,417,559 | A | 5/1995 | Schmidt |
| 5,423,535 | A | 6/1995 | Shaw et al. |
| 5,429,357 | A | 7/1995 | Kobayashi |
| 5,431,396 | A | 7/1995 | Shieh |
| 5,433,440 | A | 7/1995 | Lin |
| 5,447,307 | A | 9/1995 | Antonious |
| 5,447,309 | A | 9/1995 | Vincent |
| 5,451,056 | A | 9/1995 | Manning |
| 5,460,376 | A | 10/1995 | Schmidt et al. |
| 5,467,983 | A | 11/1995 | Chen |
| 5,470,069 | A | 11/1995 | Schmidt et al. |
| 5,474,296 | A | 12/1995 | Schmidt et al. |
| 5,482,279 | A | 1/1996 | Antonious |
| 5,497,993 | A | 3/1996 | Shan |
| 5,505,453 | A | 4/1996 | Mack |
| 5,522,593 | A | 6/1996 | Kobayashi et al. |
| 5,524,331 | A | 6/1996 | Pond |
| 5,533,729 | A | 7/1996 | Leu |
| 5,536,006 | A | 7/1996 | Shieh |
| 5,547,630 | A | 8/1996 | Schmidt |
| 5,549,297 | A | 8/1996 | Mahaffey |
| 5,564,994 | A | 10/1996 | Chang |
| 5,584,770 | A | 12/1996 | Jensen |
| 5,595,552 | A | 1/1997 | Wright et al. |
| 5,611,741 | A | 3/1997 | Schmidt et al. |
| 5,611,742 | A | 3/1997 | Kobayashi |
| D379,393 | S | 5/1997 | Kubica et al. |
| 5,626,530 | A | 5/1997 | Schmidt et al. |
| 5,643,104 | A | 7/1997 | Antonious |
| 5,643,108 | A | 7/1997 | Cheng |
| 5,643,110 | A | 7/1997 | Igarashi |
| 5,649,872 | A | 7/1997 | Antonious |
| 5,651,409 | A | 7/1997 | Sheehan |
| 5,655,976 | A | 8/1997 | Rife |
| 5,669,827 | A | 9/1997 | Nagamoto |
| 5,669,829 | A | 9/1997 | Lin |
| 5,674,132 | A | 10/1997 | Fisher |
| D387,113 | S | 12/1997 | Burrows |
| 5,695,411 | A | 12/1997 | Wright et al. |
| 5,697,855 | A * | 12/1997 | Aizawa ..................... 473/350 |
| 5,709,614 | A | 1/1998 | Horiba |
| 5,709,615 | A | 1/1998 | Liang |
| 5,711,722 | A | 1/1998 | Miyajima et al. |
| 5,716,292 | A | 2/1998 | Huang |
| 5,718,641 | A | 2/1998 | Lin |
| 5,720,673 | A | 2/1998 | Anderson |
| 5,743,813 | A | 4/1998 | Chen et al. |
| 5,753,170 | A | 5/1998 | Muang |
| 5,755,624 | A | 5/1998 | Helmstetter |
| 5,755,627 | A | 5/1998 | Yamazaki et al. |
| 5,762,567 | A | 6/1998 | Antonious |
| 5,766,092 | A | 6/1998 | Mimeur et al. |
| 5,766,094 | A | 6/1998 | Mahaffey et al. |
| 5,766,095 | A | 6/1998 | Antonious |
| 5,776,011 | A | 7/1998 | Su et al. |
| 5,807,190 | A | 9/1998 | Krumme et al. |
| 5,827,132 | A | 10/1998 | Bamber |
| RE35,955 | E | 11/1998 | Lu |
| D401,652 | S | 11/1998 | Burrows |
| 5,830,084 | A | 11/1998 | Kosmatka |
| 5,839,975 | A | 11/1998 | Lundberg |
| 5,842,934 | A | 12/1998 | Ezaki et al. |
| 5,851,159 | A | 12/1998 | Burrows |

| | | | | | |
|---|---|---|---|---|---|
| 5,863,261 A | 1/1999 | Eggiman | JP | 4020357 | 1/1992 |
| 5,873,791 A | 2/1999 | Allen | JP | 4327864 | 11/1992 |
| 5,873,795 A | 2/1999 | Wozny et al. | JP | 5212526 | 8/1993 |
| D406,294 S | 3/1999 | Burrows | JP | 05237207 | 9/1993 |
| 5,888,148 A | 3/1999 | Allen | JP | 6007487 | 1/1994 |
| 5,890,973 A | 4/1999 | Gamble | JP | 06031016 | 2/1994 |
| D411,272 S | 6/1999 | Burrows | JP | 6114126 | 4/1994 |
| 5,908,357 A | 6/1999 | Hsieh | JP | 6126002 | 5/1994 |
| 5,921,872 A | 7/1999 | Kobayashi | JP | 6154367 | 6/1994 |
| 5,931,746 A | 8/1999 | Soong | JP | 6182005 | 7/1994 |
| 5,935,019 A | 8/1999 | Yamamoto | JP | 6269518 | 9/1994 |
| 5,938,541 A | 8/1999 | Allen et al. | JP | 8168541 | 7/1996 |
| 5,941,782 A | 8/1999 | Cook | JP | 8243194 | 9/1996 |
| 5,944,619 A | 8/1999 | Cameron | JP | 8280853 | 10/1996 |
| 5,954,596 A | 9/1999 | Noble et al. | JP | 8280854 | 10/1996 |
| D415,807 S | 10/1999 | Werner et al. | JP | 8294550 | 11/1996 |
| 5,961,394 A | 10/1999 | Minabe | JP | 9028842 | 2/1997 |
| 5,967,905 A | 10/1999 | Nakahara et al. | JP | 9047531 | 2/1997 |
| 5,971,868 A | 10/1999 | Kosmatka | JP | 9154985 | 6/1997 |
| 5,993,329 A | 11/1999 | Shich | JP | 9168613 | 6/1997 |
| 5,993,331 A * | 11/1999 | Shieh .................. 473/342 | JP | 9192270 | 7/1997 |
| 6,007,432 A | 12/1999 | Kosmatka | JP | 9192273 | 7/1997 |
| 6,027,416 A | 2/2000 | Schmidt et al. | JP | 9239074 | 9/1997 |
| 6,139,445 A | 10/2000 | Werner et al. | JP | 9239075 | 9/1997 |
| 6,143,169 A | 11/2000 | Lee | JP | 9248353 | 9/1997 |
| 6,152,833 A | 11/2000 | Werner et al. | JP | 2717759 | 11/1997 |
| 6,248,025 B1 | 6/2001 | Murphy | JP | 9294833 | 11/1997 |
| 6,319,150 B1 | 11/2001 | Werner et al. | JP | 9299519 | 11/1997 |
| 6,338,683 B1 | 1/2002 | Kosmatka | JP | 10024126 | 1/1998 |
| 6,354,962 B1 | 3/2002 | Galloway et al. | JP | 10024128 | 1/1998 |
| 6,368,234 B1 | 4/2002 | Galloway | JP | 10085369 | 4/1998 |
| 6,381,828 B1 | 5/2002 | Boyce | JP | 10118227 | 5/1998 |
| 6,390,933 B1 | 5/2002 | Galloway | JP | 10137372 | 5/1998 |
| 6,398,666 B1 | 6/2002 | Evans et al. | JP | 10155943 | 6/1998 |
| 6,435,982 B1 | 8/2002 | Galloway et al. | JP | 10258142 | 9/1998 |
| 6,488,594 B1 * | 12/2002 | Card et al. .................. 473/340 | JP | 10263121 | 10/1998 |
| | | | JP | 10323410 | 12/1998 |
| | | | JP | 10337347 | 12/1998 |
| | | | JP | 2003-154040 | 5/2003 |

FOREIGN PATENT DOCUMENTS

| | | |
|---|---|---|
| GB | 2268693 A | 1/1994 |
| GB | 2331938 A | 6/1999 |
| JP | 59207169 | 11/1984 |
| JP | 61033682 | 2/1986 |
| JP | 61162967 | 7/1986 |
| JP | 6118281 | 8/1986 |
| JP | 61181477 | 8/1986 |
| JP | 61240977 | 10/1986 |
| JP | 1244770 | 9/1989 |
| JP | 02130519 | 5/1990 |

OTHER PUBLICATIONS

Golf Digest, Dec., 1981, p. 58-59.
"Variable Face Thickness Technology," Calloway Golf advertisment, undated.

* cited by examiner

METAL WOOD CLUB WITH IMPROVED HITTING FACE

CROSS-REFERENCE TO RELATED APPLICATION

The present application is a continuation-in-part of U.S. patent application Ser. No. 09/551,771 filed on Apr. 18, 2000 and now U.S. Pat. No. 6,605,007. The disclosure of the parent patent application is incorporated herein in its entirety.

FIELD OF THE INVENTION

The present invention relates to an improved golf club head. More particularly, the present invention relates to a golf club head with an improved striking face having a zone of high coefficient of restitution aligned in a predetermined orientation.

BACKGROUND

The complexities of golf club design are well known. The specifications for each component of the club (i.e., the club head, shaft, hosel, grip, and subcomponents thereof) directly impact the performance of the club. Thus, by varying the design specifications, a golf club can be tailored to have specific performance characteristics.

The design of club heads has long been studied. Among the more prominent considerations in club head design are loft, lie, face angle, horizontal face bulge, vertical face roll, face progression, face size, sole curvature, center of gravity, material selection, and overall head weight. While this basic set of criteria is generally the focus of golf club engineering, several other design aspects must also be addressed. The interior design of the club head may be tailored to achieve particular characteristics, such as the inclusion of hosel or shaft attachment means, perimeter weights on the face or body of the club head, and fillers within hollow club heads.

Golf club heads must also be strong to withstand the repeated impacts that occur during collisions between the golf club and the golf ball. The loading that occurs during this transient event can accelerate the golf ball to several orders of magnitude greater than gravity. Thus, the club face and body should be designed to resist permanent deformation or catastrophic failure by material yield or fracture. Conventional hollow metal wood drivers made from titanium typically have a uniform face thickness exceeding 0.10 inch to ensure structural integrity of the club head.

Players generally seek a metal wood driver and golf ball combination that delivers maximum distance and landing accuracy. The distance a ball travels after impact is dictated by the magnitude and direction of the ball's translational velocity and the ball's rotational velocity or spin. Environmental conditions, including atmospheric pressure, humidity, temperature, and wind speed, further influence the ball's flight. However, these environmental effects are beyond the control of the golf equipment manufacturer. Golf ball landing accuracy is driven by a number of factors as well. Some of these factors are attributed to club head design, such as center of gravity and club face flexibility.

The United States Golf Association (USGA), the governing body for the rules of golf in the United States, has specifications for the performance of golf balls. These performance specifications dictate the size and weight of a conforming golf ball. One USGA rule limits the golf ball's initial velocity after a prescribed impact to 250 feet per second ±2% (or 255 feet per second maximum initial velocity). To achieve greater golf ball travel distance, ball velocity after impact and the coefficient of restitution of the ball-club impact must be maximized while remaining within this rule.

Generally, golf ball travel distance is a function of the total kinetic energy imparted to the ball during impact with the club head, neglecting environmental effects. During impact, kinetic energy is transferred from the club and stored as elastic strain energy in the club head and as viscoelastic strain energy in the ball. After impact, the stored energy in the ball and in the club is transformed back into kinetic energy in the form of translational and rotational velocity of the ball, as well as the club. Since the collision is not perfectly elastic, a portion of energy is dissipated in club head vibration and in viscoelastic relaxation of the ball. Viscoelastic relaxation is a material property of the polymeric materials used in all manufactured golf balls.

Viscoelastic relaxation of the ball is a parasitic energy source, which is dependent upon the rate of deformation. To minimize this effect, the rate of deformation must be reduced. This may be accomplished by allowing more club face deformation during impact. Since metallic deformation may be purely elastic, the strain energy stored in the club face is returned to the ball after impact thereby increasing the ball's outbound velocity after impact.

A variety of techniques may be utilized to vary the allowable deformation of the club face, including uniform face thinning, thinned faces with ribbed stiffeners and varying thickness, among others. These designs should have sufficient structural integrity to withstand repeated impacts without permanent deformation of the club face. In general, conventional club heads also exhibit wide variations in the coefficient of restitution depending on the impact location on the face of the club. Furthermore, the accuracy of conventional clubs is highly dependent on impact location.

It has been reported in F. Werner and R. Greig, How Golf Clubs Really Works and How to Optimize Their Designs, Ch. 4, pp. 17–21 (2000) that a typical distribution of golf ball hits on the face of a driver club follows an elliptical pattern with its major axis orientating in a direction from high toe to low heel. The size of the hit distribution depends on the handicap of the golfer. Players with low handicap have smaller elliptical distribution and players with high handicap have larger elliptical distribution. These authors also patented golf clubs that have an elliptical outer hitting face that aligns in the direction of high toe to low heel. See U.S. Pat. No. 5,366,233, entitled "Golf Club Face for Drivers," issued on Nov. 22, 1994. However, there is no teaching to align the coefficient of restitution of the golf club head to the ball impact pattern.

SUMMARY OF THE INVENTION

The present invention relates to a golf club head adapted for attachment to a shaft. The head includes a hitting face and a body. The hitting face is configured and dimensioned so that it includes at least an inner zone and a concentric intermediate zone. The inner zone has relatively high flexural stiffness and the intermediate zone has lower flexural stiffness. Preferably, the inner zone has a shape that comprises a major axis and a minor axis and the major axis aligns substantially in the direction of high heel to low toe. The inner zone can have an elliptical shape or a substantially parallelogram shape. The inner zone and intermediate zone may have same shape or different shape.

This arrangement of inner and intermediate zones forms an area of relatively high flexural stiffness in the direction of high heel to low toe, thereby creating high resilience in the direction of high toe to low heel. In other words, this arrangement creates a gradient of flexural stiffness in the direction of high toe to low heel, and produces a desirable effect of manipulating resilience or higher coefficient of restitution (COR) in that direction. This area of improved coefficient of restitution advantageously coincides with the ball impact pattern that golfers typically make on the hitting face.

The inventive club head encompasses a measurement zone that exhibits high COR where the lowest COR is at least 93% of the peak COR within this measurement zone. The measurement zone is defined by a rectangle having the dimensions of 0.5 inch by 1.0 inch, and the COR values are measured at the corners of the rectangle, the mid-points of the sides and the geometric center of the rectangle. The geometric center of the measurement zone preferably coincides with the geometric center of the face of the club.

The above is accomplished by providing the inner zone with a first flexural stiffness and the intermediate zone with a second flexural stiffness. Flexural stiffness is defined as Young's modulus or elastic modulus (E) times the zone's thickness (t) cubed or $Et^3$. The first flexural stiffness is substantially higher than the second flexural stiffness. As a result, upon ball impact, the intermediate zone exhibits substantial elastic deformation to propel the ball.

In one embodiment, the first flexural stiffness is at least three times the second flexural stiffness. In other embodiments, the first flexural stiffness is six to twelve times the second flexural stiffness. More preferably, the first flexural stiffness is greater than 25,000 lb-in. Most preferably, the first flexural stiffness is greater than 55,000 lb-in. Preferably, the second flexural stiffness is less than 16,000 lb-in. More preferably, the second flexural stiffness is less than 10,000 lb-in.

Since the flexural stiffness is a function of material properties and thickness, the following techniques can be used to achieve the substantial difference between the first and second flexural stiffness: 1) different materials can be used for each portion, 2) different thicknesses can be used for each portion, or 3) different materials and thicknesses can be used for each portion.

The golf club head may further include a perimeter zone disposed between the intermediate zone and the body of the club. In one embodiment, the perimeter zone has a third flexural stiffness that is at least two times greater than the second flexural stiffness In the club heads discussed above, the inner, intermediate and optional perimeter zones can have any shape that has a major axis and a minor axis, such as elliptical, rhombus, diamond, other quadrilateral shapes with one or more rounded corners and the like. The zones may also have a substantially parallelogram shape. Furthermore, the club head inner cavities can have a volume greater than about 100 cubic centimeters, and more preferably a volume greater than about 300 cubic centimeters. In other words, the club head in accordance to the present invention can be used in driver clubs and/or fairway clubs. In addition, the inner, intermediate, and perimeter zones can each have variable thickness.

Another feature of the present invention is locating the center of gravity of the club head with respect to a Cartesian coordinate system. The origin of the Cartesian coordinate system preferably coincides with the geometric center of the hitting face. The X-axis is a horizontal axis positioned tangent to the geometric center of the hitting face with the positive direction toward the heel of the club. The Y-axis is another horizontal axis orthogonal to the X-axis with the positive direction toward the rear of the club. The Z-axis is a vertical axis orthogonal to both the X-axis and Y-axis with the positive direction toward the crown of the club. The center of gravity is preferably located behind and lower than the geometric center of the face.

In one preferred embodiment, the center of gravity is spaced from the geometric center along the Z-axis by about −0.050 inch to about −0.150 inch, and more preferably by about −0.110 inch. The center of gravity is preferably spaced about ±0.050 inch, and more preferably about +0.015 inch from the geometric center along the X-axis. The center of gravity is preferably spaced about +2.0 inches and more preferably about +1.35 inches from the geometric center along the Y-axis.

The hitting face may comprise a face insert and a face support. The face support defines a cavity adapted to receive the face insert. The hitting face may further comprise at least one side wall, which can be a partial crown portion or a partial sole portion. Preferably, the inner zone is located on the face insert, and the intermediate zone may partially be located on the face insert and partially on the face support.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENT

Figure 5:
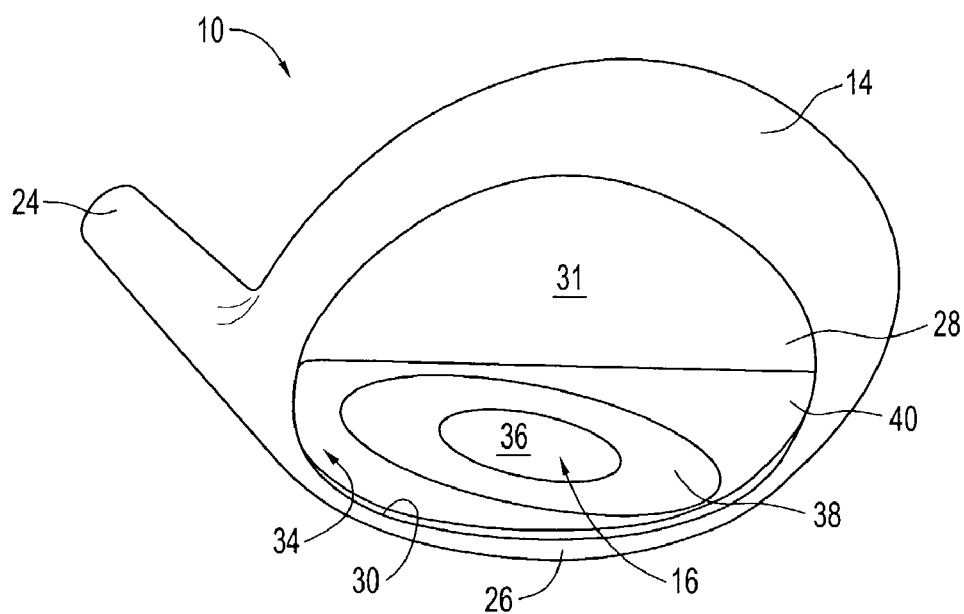
FIG. 5 is a bottom, perspective view of the golf club head of FIG. 1.

Referring to FIGS. 1–5, a first embodiment of a golf club head 10 of the present invention is shown. Club head 10 includes shell 12 with body 14, hitting face 16, toe portion 18, heel portion 20, sole plate 22, hosel 24, bottom portion 26, crown portion 28, and rear portion 29. The sole plate 22 fits in a recess 30 (as shown in FIG. 5) in the bottom portion 26 of body 14. The shell 12 and sole plate 22 create an inner cavity 31 (as shown in FIG. 5). The hitting face 16 has an exterior surface 32 and an interior surface 34. The exterior surface 32 is generally smooth except for external grooves (which are omitted for clarity). Preferably, interior surface 34 has elevated or depressed areas to accommodate the varying thickness of hitting face, as discussed below and shown in FIGS. 3A–3D.

A golf club shaft (not shown) is attached at hosel 24 and is disposed along a shaft axis SHA. The hosel may extend to the bottom of the club head or may terminate at a location between the top and bottom portions of the head. The hosel can also terminate flush with the top portion or extend into the cavity within the head.

Inner cavity 31 of club head 10 may be empty, or alternatively may be filled with foam or other low specific gravity material. It is preferred that the inner cavity 31 has a volume greater than 100 cubic centimeters, and more preferably greater than 300 cubic centimeters. In other words, the club head design in accordance to the present invention can be used with any driver club, as well as any fairway club. Preferably, the mass of the inventive club head is greater than 150 grams but less than 250 grams.

Figure 1:
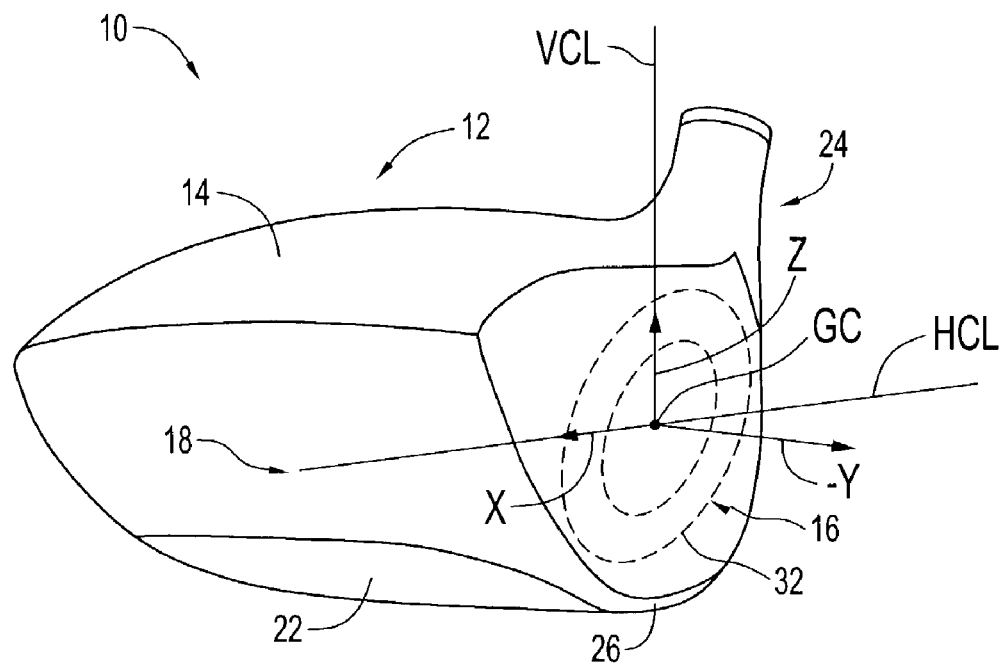
FIG. 1 is a toe side, front, perspective view of an embodiment of a golf club head of the present invention.
Figure 2:
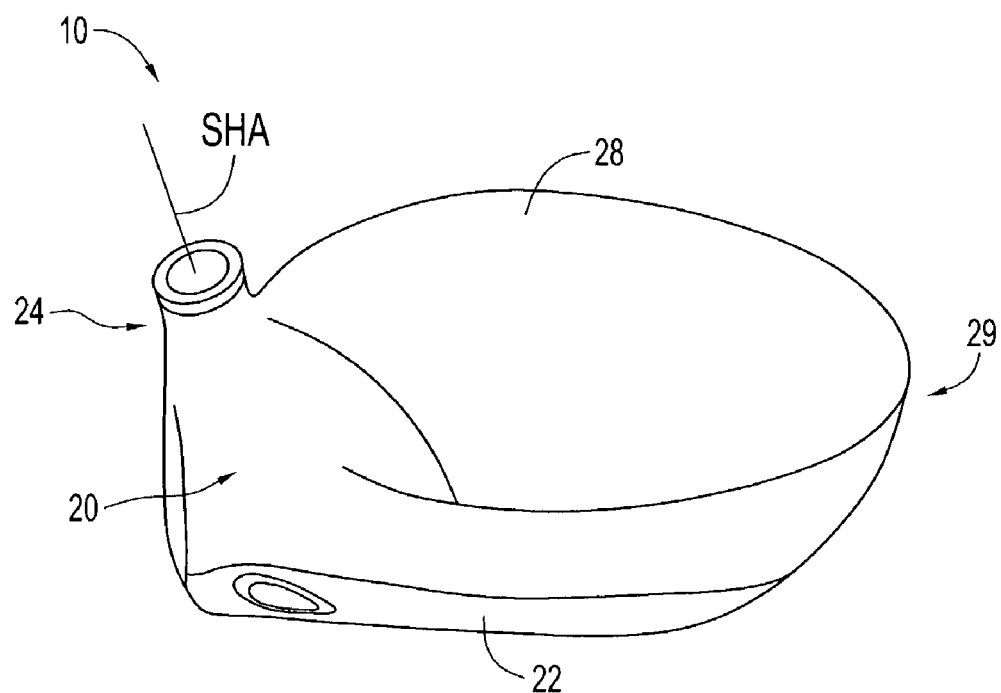
FIG. 2 is a heel side, rear, perspective view of the golf club head of FIG. 1.
Figure 3:
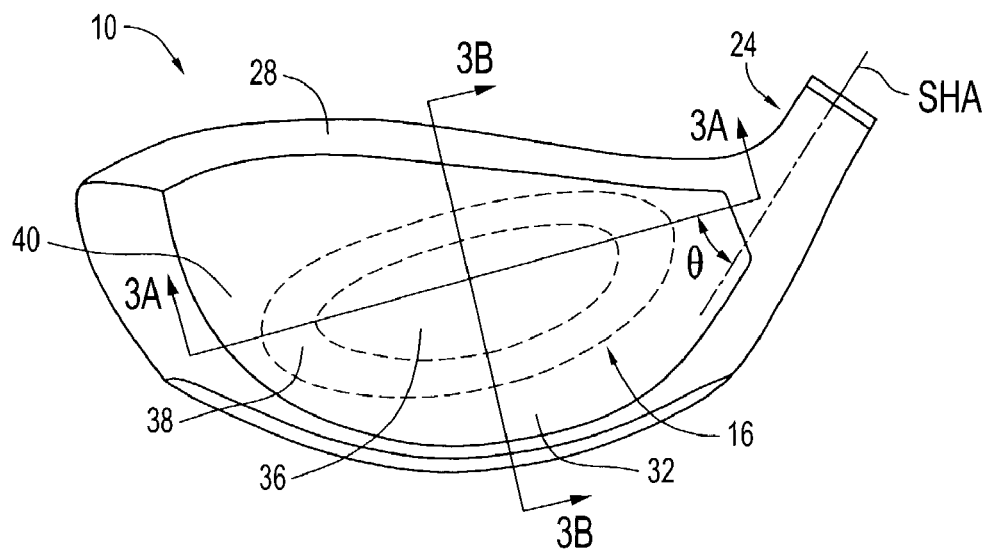
FIG. 3 is a front, elevational view of the golf club head of FIG. 1.
Figure 3A:
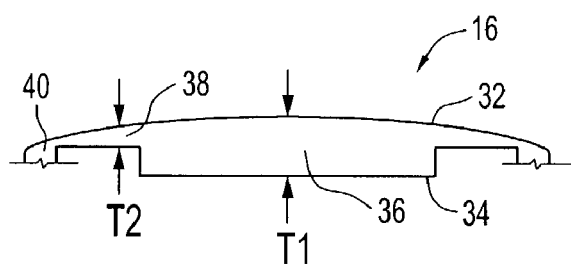
FIG. 3A is a cross-sectional view of the face of the golf club head of FIG. 1 along line 3A—3A.
Figure 3B:
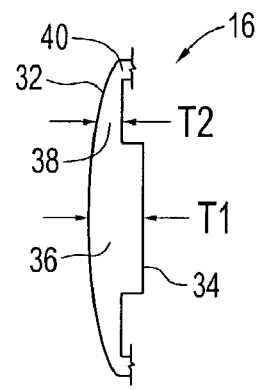
FIG. 3B shows a cross-sectional view the face of the golf club head of FIG. 1 along line 3B—3B.
Figure 3C:
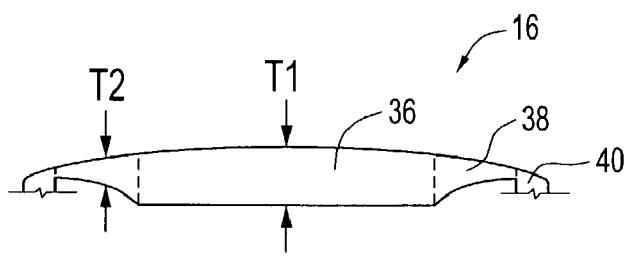
FIGS. 3C and 3D are alternative embodiments of FIGS. 3A and 3B, respectively.
Figure 3D:
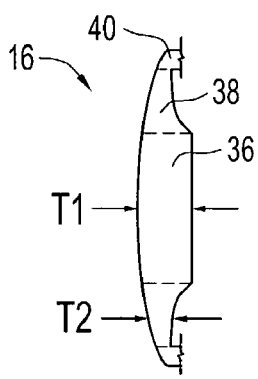
Figure 4:
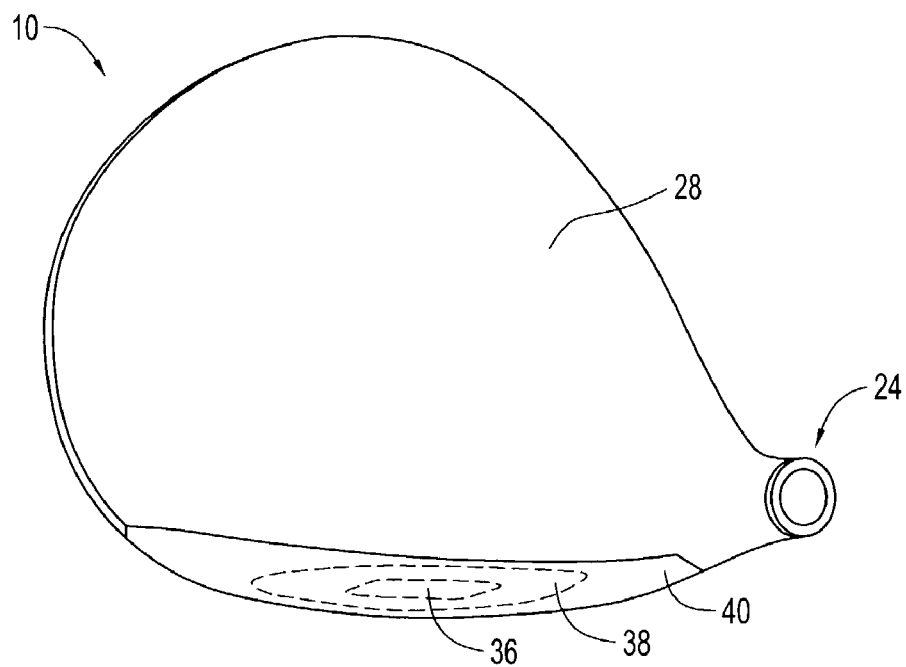
FIG. 4 is a top view of the golf club head of FIG. 1.

Referring to FIGS. 1 and 3–3D, the face 16 includes an inner zone or portion 36, an intermediate zone or surrounding portion 38 adjacent the inner zone 36, and an optional perimeter zone or outer portion 40. The intermediate zone 38 preferably surrounds inner zone 36, and the perimeter zone 40 preferably surrounds the intermediate zone 38. The inner zone 36 is a contiguous zone located on the hitting face 16 and contains a geometric center ("GC") of the hitting face. As shown, inner zone 36 and its concentric zones have a generally elliptical shape with a major axis in the direction of high heel to low toe. As used herein, the term "ellipse" or "elliptical" refers to non-circular shapes that have discernable major axis and minor axis, and include, but are not limited to, any quadrilateral shapes, geometrical ellipses, quadrilateral shapes with one or more rounded corner(s) and unsymmetrical elliptical shapes. Also, the term "concentric" refers to shapes that substantially encircle or surround other shapes. The "major axis" is defined as the axis coinciding with the longest length that can be drawn through the non-circular shapes without intersecting the perimeter of the shapes at more than two locations, i.e., at the start and end points of said length. The "minor axis" is orthogonal to the major axis at or near its midpoint.

The major axis of inner portion 36 forms an angle, θ, with the shaft axis, SHA. Preferably, angle θ is between about 10° to about 60°, more preferably between about 20° and about 50°, and most preferably between about 25° and about 45°. Additionally, the ratio of the length of the major axis to the length of minor axis is preferably greater than 1.0 and more preferably less than about 6.0.

Preferably, zones 36, 38 and 40 are concentric to each other within hitting face 16. The inner zone 36 has a first thickness $T_1$. The intermediate zone 38 has a second thickness $T_2$. The first thickness $T_1$ is greater than the second thickness $T_2$. Typically, when the club head is cast, the perimeter zone 40 is thicker than the intermediate zone 38. Alternatively, the hitting face may also be forged. However, the present invention is not limited to any manufacturing technique. $T_1$ may range from about 1.5 mm to about 7.5 mm and $T_2$ may range from about 0.8 mm to about 3.0 mm. Preferably, the first thickness $T_1$ is equal to about one and a half (1.5) times the thickness $T_2$ to about four (4) times the thickness $T_2$.

The thickness relationships between the zones 36, 38, and 40 are provided so that a predetermined relationship exists between flexural stiffness exhibited by each of the zones. For clubs that have a hitting face made from a single material, such as titanium or titanium alloy, the area of highest thickness corresponds to the portion with the highest flexural stiffness. Flexural stiffness (FS) of each portion is defined as:

$$FS = E(t^3),$$

where E is the elastic modulus or Young's modulus of the material of the portion and t is the thickness of the portion. Young's modulus of titanium is about $16.5 \times 10^6$ lbs/in$^2$, and thickness is typically measured in inch. Hence, FS as used in this application has the unit of lb·in.

The inner zone 36 has a first flexural stiffness $FS_1$. The intermediate zone 38 has a second flexural stiffness $FS_2$. The perimeter zone 40 has a third flexural stiffness $FS_3$. The predetermined relationship between the portions is that the first flexural stiffness $FS_1$ is substantially greater than the second flexural stiffness $FS_2$, and the optional third flexural stiffness $FS_3$ is substantially greater than the second flexural stiffness $FS_2$. Preferably, the first flexural stiffness $FS_1$ is at least three times greater than the second flexural stiffness $FS_2$, i.e., $(FS_1/FS_2) \geq 3$. When the above ratio of flexural stiffness is less than three, the inner zone sustains excessive deformation during impact and accuracy of the club is diminished. More preferably, the first flexural stiffness $FS_1$ is about six (6) to twelve (12) times greater than the second flexural stiffness $FS_2$. Most preferably, the first flexural stiffness $FS_1$ is about eight (8) times greater than the second flexural stiffness $FS_2$. Preferably, the third flexural stiffness $FS_3$ is at least two times greater than the second flexural stiffness $FS_2$, i.e., $(FS_3/FS_2) \geq 2$.

Alternatively, the flexural stiffness, $FS_1$, $FS_2$ or $FS_3$, can be determined for two combined adjacent zones, so long as the preferred ratio $(FS_1/FS_2) \geq 3$ or $(FS_3/FS_2) \geq 2$ is satisfied. For example, $FS_1$ can be calculated to include both zones 36 and 38, and $FS_3$ can be calculated to include both zones 38 and 40.

The thickness of the zones, $T_1$ and $T_2$, may be constant within the zone as illustrated in FIGS. 3A and 3B, or may vary within the zone as illustrated in FIGS. 3C and 3D. For the purpose of determining FS, when the thickness varies, a weighted average thickness is calculated. The determination of FS when the thickness varies or when the material is anisotropic is fully discussed in the parent patent application, which has already been incorporated by reference in its entirety.

In club head 10 (as shown in FIGS. 3–3D), the above flexural stiffness relationships are achieved by selecting a certain material with a particular elastic modulus and varying the thickness of the zones. In another embodiment, the flexural stiffness relationships can be achieved by varying the materials of the zones with respect to one another so that the zones have different elastic moduli and the thickness is changed accordingly. Thus, the thickness of the zones can be the same or different depending on the elastic modulus of the material of each zone. It is also possible to obtain the required flexural stiffness ratio through the use of structural ribs, reinforcing plates, and thickness parameters.

Quantitatively, it is preferred that the first flexural stiffness $FS_1$ is greater than 25,000 lb·in. When the first flexural stiffness is less than 25,000 lb·in excessive deformation of the inner region can occur during impact and accuracy is diminished. More preferably, the first flexural stiffness $FS_1$ is greater than 55,000 lb·in. Preferably, the second flexural stiffness $FS_2$ is less than 16,000 lb-in. When the second flexural stiffness is greater than 16,000 lb-in, the resultant ball velocity is reduced. More preferably, the second flexural stiffness $FS_2$ is less than 10,000 lb-in and, most preferably, less than 7,000 lb-in.

Referring to FIG. 3, it is preferred that inner zone 36 has an area that is between about 15% and about 60% of the exterior surface area 32. The percentage of face area is computed by dividing the area of each zone 36, 38, or 40 by the total face area of exterior surface 32. It should be noted that the face area of exterior surface 32 is equivalent to the total area of zones 36, 38, and 40. When the inner zone 36 is less than 15% of the total face area, then accuracy can be diminished. When inner portion 36 is greater than 60% of the face area 32, then the coefficient of restitution can be diminished.

Referring again to FIG. 1, the club head 10 is further formed so that a center of gravity of the club head has a predetermined relationship with respect to a Cartesian coordinate system with its center located on hitting face 16 and coincident with the geometric center GC of the face 16. The hitting face 16 includes a vertical centerline VCL and a horizontal centerline HCL perpendicular thereto. The geometric center (GC) of hitting face 16 is located at the intersection of centerlines VCL and HCL. The VCL and HCL are co-linear with the X-axis and the Z-axis of a Cartesian coordinate system, described below. Preferably, the GC of the inner zone 36 is spaced from the GC of hitting face 16 by a distance of less than about 0.10 inch, more preferably less than about 0.05 inch and most preferably less than about 0.025 inch. The GC of inner zone 36 may be coincident with the GC of hitting face 16. The GC of inner zone 36 can be defined as the intersection between the major axis and the minor axis of the zone.

The Cartesian coordinate system is defined as having the origin coincident with the geometric center of the hitting face. The hitting face is not a rectilinear plane, but due to the bulge and roll radii it is a curvilinear surface. The X-axis is a horizontal axis lying tangent to the geometric center of the hitting face with the positive direction toward the heel of the club. The Y-axis is another horizontal axis orthogonal to the X-axis with the positive direction toward the rear of the club. The Z-axis is a vertical axis orthogonal to both the X-axis and Y-axis with the positive direction toward the crown of the club.

The center of gravity is preferably located behind and lower than the geometric center of the face when the club head is resting on a flat surface (i.e., at its natural loft). In one preferred embodiment, the center of gravity of club head 10 is spaced from the geometric center along the Z-axis between about −0.050 inch and about −0.150 inch, more preferably about −0.110 inch. The center of gravity is preferably spaced about ±0.050 inch, more preferably about 0.015 inch, from the geometric center along the X-axis. The center of gravity is preferably spaced about 2.0 inches or less and more preferably about 1.35 inches or less from the geometric center along the Y-axis.

The center of gravity for the club head can be achieved by controlling the configuration and dimensions of the club head in addition to adding predetermined weights to the sole plate or to the club head. Other known methods of weight manipulation can be used to achieve the inventive center of gravity location as set forth above.

Figure 6:
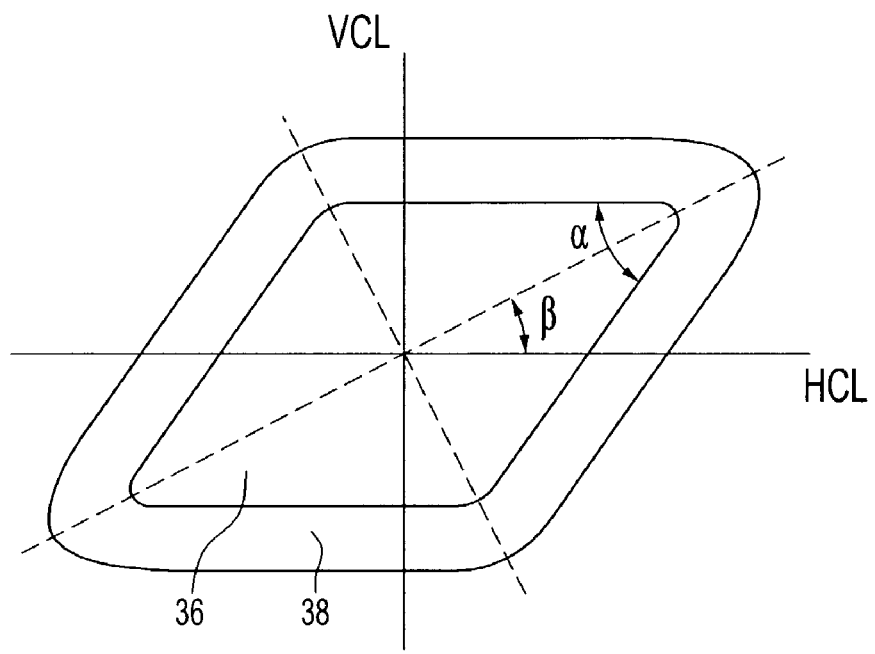
FIG. 6 is a schematic view of substantially parallelogram shaped the inner and intermediate zones.

FIG. 6 illustrates another embodiment of the present invention. Central zone 36 has a generally parallelogram shape, such that the opposite sides are generally parallel and the angles formed between adjacent sides are rounded. More specifically, the acute angle α of central zone 36 is preferably between 40° and 85°. Additionally, the major axis of central zone 36, as shown, forms an angle β with the HCL, which preferably is between 5° and 45°. The major axis is the line connecting the two acute angles of the parallelogram. Similar to the embodiments disclosed above, intermediate zone 38 surrounds central zone 36, and the relative thickness and ratio of FS between zone 36 and zone 38 follow the relationships discussed above.

Figure 7:
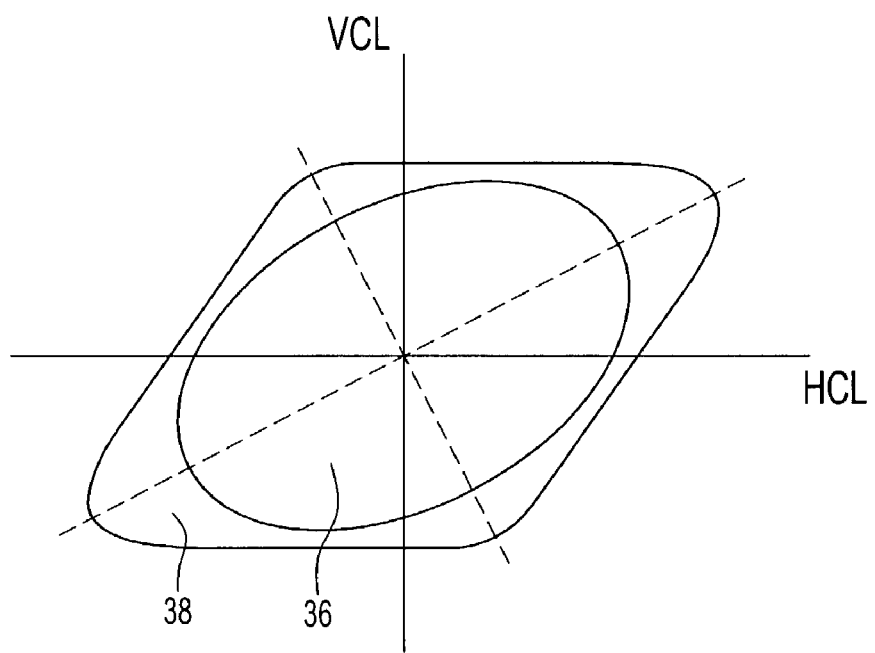
FIG. 7 is a schematic view of the inner and intermediate zones with substantially parallelogram and elliptical shape.

As shown in FIG. 7, central zone 36 can be an ellipse while intermediate zone 38 can have a generally parallelogram shape. Conversely, central zone 36 can have a generally parallelogram shape, while intermediate zone 38 can be an ellipse. Furthermore, as illustrated intermediate zone 38 may have varying width.

Figure 8:
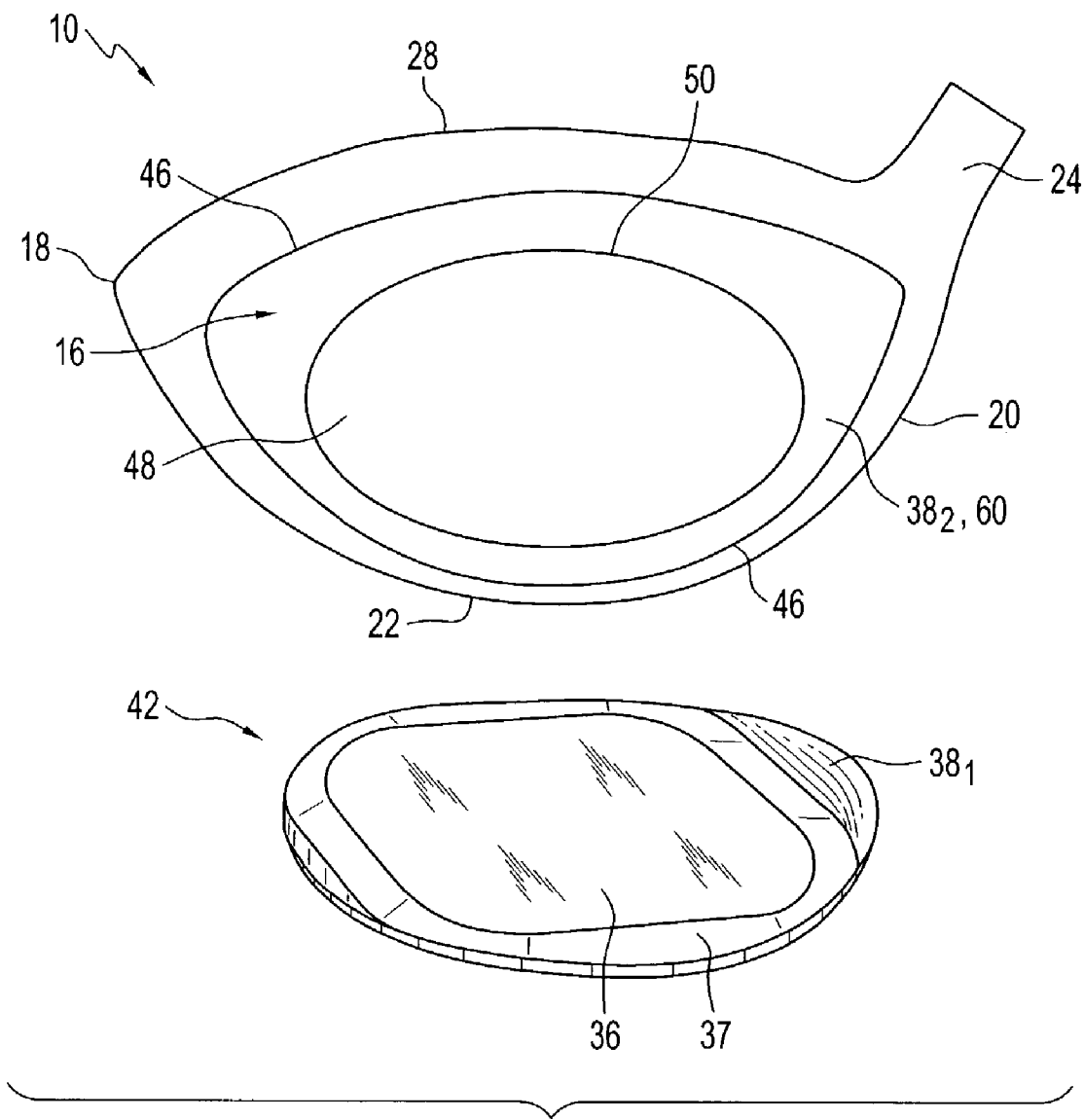
FIG. 8 is a front, exploded view of another embodiment of the present invention.

In accordance to another aspect of the present invention, hitting face 16 may comprise a face insert 42 and face support 44, as shown in FIG. 8. In this embodiment, hitting face 16 is delineated from crown 28, toe 18, sole 22 and heel 20 by parting line 46. Central zone 36 is preferably disposed on the back side of face insert 42, and, as shown, has a generally parallelogram shape. Intermediate zone 38, designated as $38_1$ and $38_2$, can be disposed partially on face insert 42 and partially on face support 44. A transition zone 37 having variable thickness is disposed between central zone 36 and intermediate zone 38. Preferably, the thickness of central zone 36 is reduced to the lesser thickness of intermediate zone 38 within transition zone 37. This reduces any local stress-strain caused by impacts with golf balls due to abrupt changes in thickness. Face support 44 defines hole 48, which is bordered by rim 50. Face insert 42 can be attached to face support 44 by welding at or around rim 50. For the purpose of determining the FS ratio for this embodiment, the $FS_1$ of the inner zone includes both zone 36 and zone 37.

Figure 9:
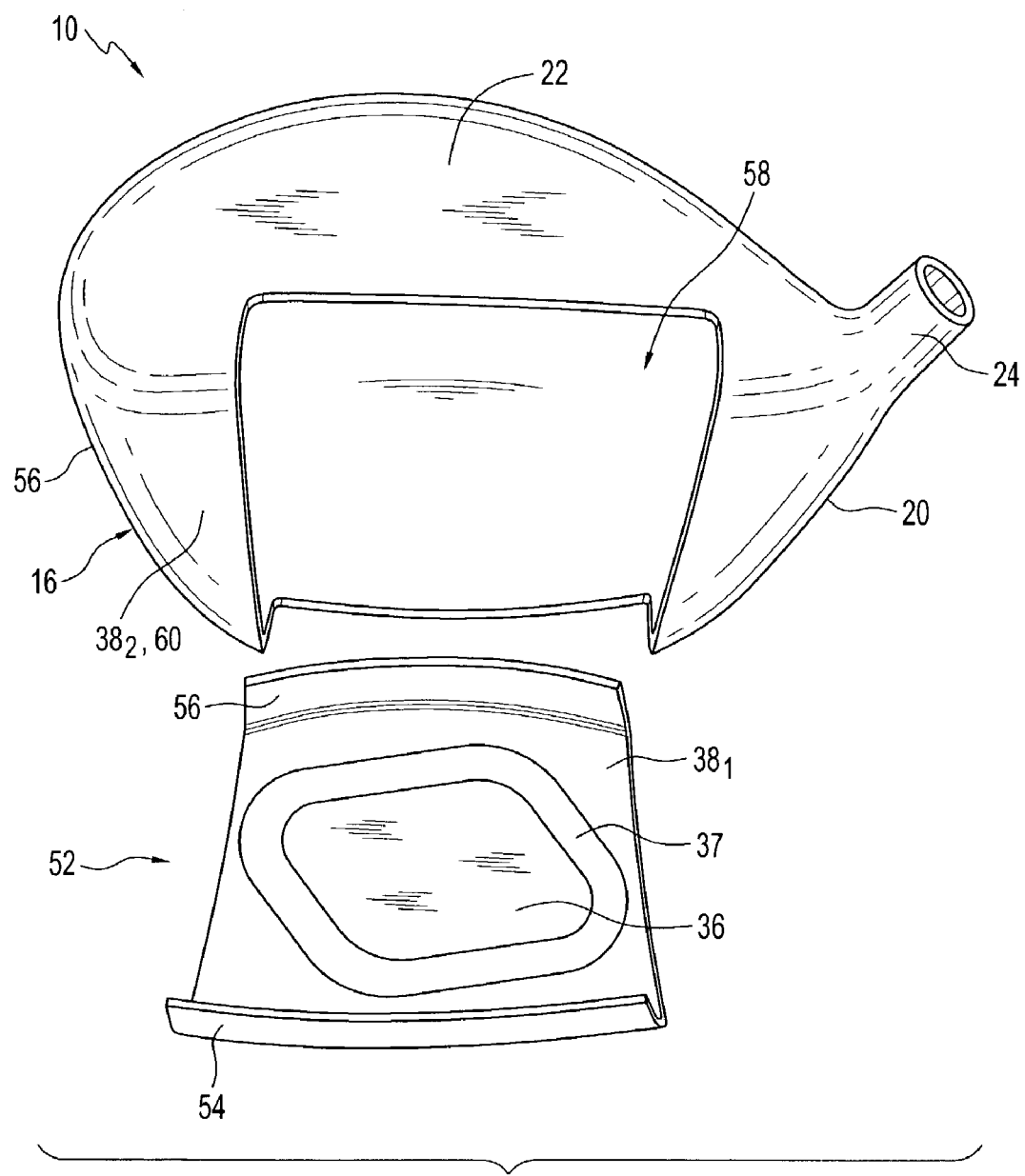
FIG. 9 is a front, exploded view of another embodiment of the present invention.

In accordance to another aspect of the invention, the face insert may include one or more side walls, wherein the side walls may form part of the crown and/or part of the sole. As shown in FIG. 9, face insert 52 comprises central zone 36, transition zone 37, a portion of intermediate zone 38, partial crown portion 54 and partial sole portion 56. Club head 10 correspondingly defines cavity 58 sized and dimensioned to receive face insert 52. Face insert 52 is preferably welded to club head 10. Face insert 52 together with face support 60 forms hitting face 16. Similar to the embodiment illustrated in FIG. 8, intermediate zone 38, designated as $38_1$, and $38_2$, can be disposed partially on face insert 52 and partially on face support 60.

EXAMPLE

Figure 10A:
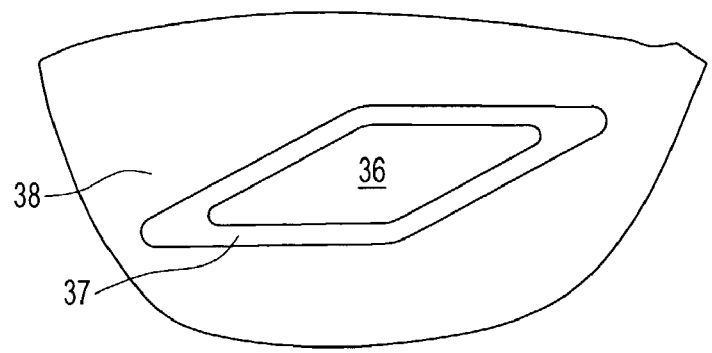
FIGS. 10(a)–10(c) illustrate the results from a comparative example, which compares iso-COR contour lines of conventional golf club head and of an embodiment of the present invention.

In this example, hitting face 16 has the following construction. The central zone 36 has a substantially parallelogram shape, as shown in FIG. 10(a), with a major axis measuring about 3 inches and a minor axis about 0.75 inches with a thickness $T_1$, of about 0.120 inch. The central zone 36 has a concentric transition zone 37 with a similar shape as the central zone 36. The intermediate zone 38 surrounds the central and transition zones with a thickness $T_2$ of 0.080 inch and comprises the remainder of the face hitting area. There is no perimeter zone 40 included in this example. The major axis of zone 36 substantially coincides with the major axis of zone 38, and these two major axes form angle theta (θ) of about 50° with the shaft axis. Furthermore, zones 36 and 37 comprise about 18% of the total face surface area. A single homogeneous material, preferably a titanium alloy, with a Young's modulus (E) of approximately $16.5 \times 10^6$ lbs/in$^2$ is used. In this example, the (FS1/FS2) ratio is 3.4 when FS1 includes both zones 36 and 37 and FS2 includes zone 38.

The test results were generated using computational techniques, which include finite element analysis models. In the computer model, the following assumptions were made: club head loft of 9°; club head mass of 195 grams; and club head material is 6AL-4V titanium alloy. The golf ball used in the model was a two-piece solid ball. Finite element models were used to predict ball launch conditions and a trajectory model was used to predict distance and landing area. The impact condition used for club coefficient of restitution (COR) tests was consistent with the USGA Rules for Golf, specifically, Rule 4-1e Appendix II Revision 2 dated Feb. 8, 1999.

Figure 10B:
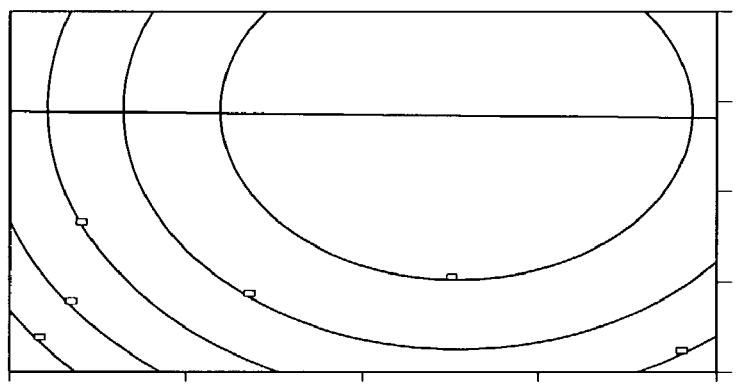
Figure 10C:
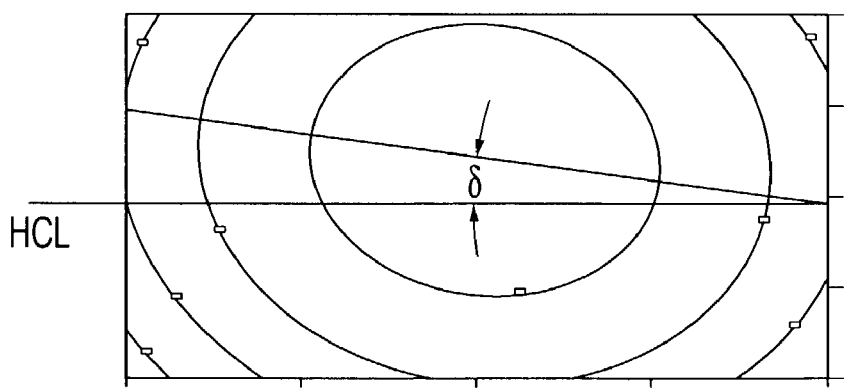

Distributions of coefficient of restitution (COR) are shown in FIGS. 10(b) and 10(c). The lines indicate contour lines, similar to the contour lines in topography maps or weather maps, and indicate lines of constant COR (hereinafter iso-COR lines). The innermost contour line indicates the highest COR region on the hitting face and outer contour lines indicate lower COR regions on the hitting face. FIG. 10(b) represents the iso-COR contours for a conventional club having a hitting face with uniform thickness, and FIG. 10(c) represents the iso-COR contours of the inventive club described in this Example.

COR or coefficient of restitution is one way of measuring ball resiliency. COR is the ratio of the velocity of separation to the velocity of approach. In this model, therefore, COR was determined using the following formula:

$$(v_{club\text{-}post} - v_{ball\text{-}post})/(v_{ball\text{-}pre} - v_{club\text{-}pre})$$

where, $v_{club\text{-}post}$ represents the velocity of the club after impact;
$v_{ball\text{-}post}$ represents the velocity of the ball after impact;
$v_{club\text{-}pre}$ represents the velocity of the club before impact (a value of zero for USGA COR conditions); and
$v_{ball\text{-}post}$ represents the velocity of the ball before impact.

COR, in general, depends on the shape and material properties of the colliding bodies. A perfectly elastic impact has a COR of one (1.0), indicating that no energy is lost, while a perfectly inelastic or perfectly plastic impact has a COR of zero (0.0), indicating that the colliding bodies did not separate after impact resulting in a maximum loss of energy. Consequently, high COR values are indicative of greater ball velocity and distance.

The iso-COR contour lines generated by the computational analysis are shown within a rectangle having dimensions of 0.5 inch by 1.0 inch, as typically used in the art. Within this rectangle, the inventive club head exhibits relatively high and substantially uniform COR values. The COR values are measured at nine points within this rectangle, i.e., the corners of the rectangle, mid-points of the sides and the geometric center of the rectangle. Additionally, the geometric center of this rectangular measurement zone preferably coincides with the geometric center of the hitting face of the club. In this example, the lowest COR within this measurement zone is 0.828 and the peak COR is 0.865. According to the present invention, the lowest COR is within 93% of the peak COR. This advantageously produces a hitting face with a substantially uniform COR and large "sweet spot".

The iso-COR contour lines of the conventional club shown in FIG. 10(b) follow a substantially elliptical pattern. Furthermore, the center of the innermost iso-COR contour line, which has the highest COR value, is offset from the geometric center of the rectangular measurement zone, indicating a reduction in COR. The major axis of these contour lines is substantially horizontal.

The iso-COR contour lines for the inventive club also follow an elliptical pattern, and as shown in FIG. 10(c), the major axis of the pattern does not coincide with the horizontal center line, HCL, of the hitting face. The test results indicate that the major axis of the iso-COR pattern makes an angle, delta(δ), with the HCL. The angle δ is at least 5°, and more preferably at least 7° in the direction from high toe to low heel. While the major axis of central zone 36 with the highest FS runs substantially from high heel to low toe, the major axis of the iso-COR contours runs substantially in a different direction, i.e., from high toe to low heel, which advantageously coincides with the typical hit distribution that golfers make on the hitting face, discussed above. Furthermore, the center of the innermost iso-COR contour line is closer to the geometrical center of the rectangular measurement zone, indicating a higher peak COR value.

Without being limited to any particular theory, the inventors of the present invention observe that when an elliptical area of high thickness or high FS is present at or near the center of the hitting face with areas of less thickness or lower FS surrounding it, the iso-COR contour lines generally form an elliptical shape where the major axis of the iso-COR contours forms an angle with the major axis of the areas of high thickness or high FS. This arrangement of inner and intermediate zones forms a zone of relatively high flexural stiffness in the direction of high heel to low toe thereby creating high resilience in the direction of high toe to low heel. In other words, this arrangement creates a gradient of flexural stiffness in the direction of high toe to low heel and produces a desirable effect of manipulating resilience or higher coefficient of restitution (COR) in that direction. This area of improved coefficient of restitution advantageously coincides with the ball impact pattern that golfers typically make on the hitting face.

While various descriptions of the present invention are described above, it should be understood that the various features of each embodiment can be used alone or in any combination thereof. Therefore, this invention is not to be limited to only the specifically preferred embodiments depicted herein. Further, it should be understood that variations and modifications within the spirit and scope of the invention may occur to those skilled in the art to which the invention pertains. For example, the face and/or individual zones can have thickness variations in a step-wise or continuous fashion. Other modifications include a perimeter zone that has a thickness that is greater than or less than the adjacent, intermediate zone. In addition, the shapes of the central, intermediate, and perimeter zones are not limited to those disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

We claim:

1. A golf club head comprising:
   a face insert and a face support,
   the face insert and the face support form a hitting face;
   the hitting face comprises an inner zone having a generally parallelogram shape;
   the hitting face comprises a first flexural stiffness having a major axis that aligns substantially in the direction of high heel to low toe and an intermediate zone having a second flexural stiffness, wherein the first flexural stiffness is higher than the second flexural stiffness and wherein the major axis of the parallelogram inner zone forms a first angle in the range of about 10° to about 60° with a shaft axis of the club head.

2. The golf club head of claim 1, wherein the face support defines a cavity sized and dimensioned to receive the face insert.

3. The golf club head of claim 2, wherein said cavity is located on the hitting face.

4. The golf club head of claim 1, wherein the golf club head defines a cavity sized and dimensioned to receive the face insert.

5. The golf club head of claim 1, wherein the face insert comprises at least one side wall.

6. The golf club head of claim 5, wherein the at least one side wall is a partial crown portion.

7. The golf club head of claim 5, wherein the at least one side wall is a partial sole portion.

8. The golf club of claim 1, wherein the first angle is about 20° to about 50°.

9. The golf club of claim 1, wherein the first angle is about 25° to about 45°.

* * * * *